United States Patent [19]

Sorge

[11] Patent Number: 5,347,075
[45] Date of Patent: * Sep. 13, 1994

[54] MUTAGENESIS TESTING USING TRANSGENIC NON-HUMAN ANIMALS CARRYING TEST DNA SEQUENCES

[75] Inventor: Joseph A. Sorge, San Diego, Calif.

[73] Assignee: Stratagene, La Jolla, Calif.

[ * ] Notice: The portion of the term of this patent subsequent to Sep. 18, 2009 has been disclaimed.

[21] Appl. No.: 711,332

[22] Filed: Jun. 6, 1991

Related U.S. Application Data

[63] Continuation of Ser. No. 45,037, May 1, 1987, abandoned.

[51] Int. Cl.$^5$ ............................................. C12N 15/00
[52] U.S. Cl. ................... 800/2; 800/DIG. 1; 435/172.3; 435/320.1; 435/317.1; 424/2; 424/9; 935/31; 935/72; 935/73; 935/111
[58] Field of Search ............................ 800/2, DIG. 1; 435/172.3, 320.1, 317.1; 424/2, 9; 935/31, 72, 73, 111

[56] References Cited

U.S. PATENT DOCUMENTS 4,736,866  4/1988  Leder et al. ........................ 800/2

OTHER PUBLICATIONS

Tice et al., "Modern Biological Theories of Aging" Warner et al., eds, p. 214, Raven Press (1987).
Palmiter et al., Cell 41: 343–345 (1985).
Glazer et al., Proc. Natl. Acad. Sci. 83: 1041–1044 (1986).
Singh et al., Canadian J. Genet. & Cytology 28: 286–293 (1986).
Lohman et al., Mutation Res. 181: 227–234 (1987).
Summers et al., Mutation Res. 220: 263–268 (1989).

*Primary Examiner*—Jasemine C. Chambers

[57] ABSTRACT

An assay for monitoring and assessing the mutagenic potential of agents which involves creating transgenic non-human animals carrying a test DNA sequence or sequences that can be quickly recovered and examined for mutations following exposure to one or more suspected mutagenic agents.

3 Claims, 2 Drawing Sheets

Figure 1

MOUSE LAMBDA               LAMBDA MOUSE

----/========cos====Test DNA Sequence====cos-------/-----

DNA       DNA               DNA         DNA

↓          add lambda

↓          packaging extract cos=======Test DNA Sequence ====cos

/

↓          infect E. coli look for changes in Test DNA Sequence in E. coli

MUTAGENESIS TESTING USING TRANSGENIC NON-HUMAN ANIMALS CARRYING TEST DNA SEQUENCES

This is a continuation of application Ser. No. 07/045,037, filed May 1, 1987, now abandoned.

BACKGROUND OF THE INVENTION

1. Field of the Invention

This invention pertains to tests for monitoring mutagenic agents and to transgenic animals. More specifically, the invention relates to genotypic changes in live animals that are monitored by the creation and use of transgenic non-human animals carrying marker DNA sequences that can be quickly recovered and examined for mutations.

2. Description of Related Art

Various agents, such as radiation, ultraviolet light, synthetic chemicals, natural substances, and aberrations in genetic replication and repair can produce mutations in DNA. Whenever a new chemical, drug, or food additive, for example, is to be taken from the laboratory to the marketplace, it must be tested for its toxicity and cancer-causing potential. Existing tests that assess the mutagenic potential of substances focus either on alterations of DNA in cultured cells or alterations in the health of test animals. Unfortunately, few tests that monitor alterations in DNA actually expose live animals to the agent to be tested. This is because it is very difficult to rapidly monitor small alterations in the genetic code simultaneously in many different organs. Tests to detect these mutations must be very sensitive. They must be able to detect a single mutation amongst millions of normal genetic units. The difficulty of this task currently makes this approach prohibitively expensive for live animal studies. Therefore, most current live animal toxicity tests use disease formation or large scale chromosomal alterations as an assay for gene alteration.

The problem of detecting small scale DNA alterations that are caused by potential mutagenic agents has generally been approached by performing studies on cells in culture (in vitro tests). The well-known Ame's test uses a special strain of bacteria to detect these mutation. Ames, et al., An Improved Bacterial Test System for the Detection and Classification of Mutagens and Carcinogens, *Proc. Nat. Acad. Sci.* 70:782–86 (1973). This test and many analogues that use other types of bacterial or animal cells permit the rapid screening of very large numbers of cells for the appearance of an altered phenotype. The appearance of this altered phenotypic trait reflects the occurrence of a mutation within the test gene. These tests are, however, insensitive to or nonspecific for many mutagens that result from metabolic activation of the agent being screened. Although attempts have been made to increase their sensitivity and specificity by activation of such metabolites with liver and other extracts it is noted that, for instance, the metabolites produced by these extracts are often not present at the same concentration as in the live tissues of an animal. Metabolites that are only produced in other organs are not detected at all.

Eukaryotic cell lines have also been used to detect mutations. E.g., Glazer et al., Detection and Analysis of UV-induced Mutations in Mammalian Cell DNA using Lambda Phage Shuttle Vector., *Proc. Natl. Acad. Sci. USA* 83:1041–1044 (1986). In this test a target test gene, the amber suppressor tyrosine tRNA gene of *E. coli* in a bacteriophage shuttle vector, was integrated into a genomic host mammalian cell line by DNA transfection. After exposing the host cell line to putative mutagenic agents, test genes were re-isolated, propagated in bacteria, and analyzed for mutations. Because the host is only a mammalian cell line and not a live animal, the test is incapable of accurately monitoring mutagenic metabolites of the agent being tested that are only produced at the appropriate concentrations by differentiated cells or the tissue of live animals.

Such test genes and large scale screening assays are not available for live animal studies. Short of relying on longterm animal studies that detect phenotypic changes that require a long time to be identifiable, such as tumors, organ failure, etc., current tests do not provide a means for monitoring organ-specific mutations of DNA. Hence, there exists a need for a system that places a test DNA sequence within an animal and is subsequently assayed on a large scale for mutations. There also exists a need for a test that detects mutations caused by chemical metabolites of the agent being tested. To be most effective the system needs to be capable of monitoring small genetic changes in as many tissues of an animal and as easily, rapidly, and inexpensively as possible.

The present invention produces a test that satisfies these needs. The test is a sensitive screen for the mutagenicity of all agents. The test not only monitors the mutagenic effects of the agent being screened it also monitors the mutagenic effects of all metabolites that occur in animal tissues of the agent being tested. It permits the identification of the nature of the mutation: e.g., DNA transition, transversion, deletion, or a point or frameshift mutation. The test is rapid and it is inexpensive relative to other tests. And, it will spot a potential mutagen rapidly before other more expensive tests can be completed.

BRIEF DESCRIPTION OF THE DRAWINGS

In the drawings, forming a portion of this disclosure:

FIG. 1 illustrates the sequence of process steps for performing the invention.

SUMMARY OF THE INVENTION

Figure 2:
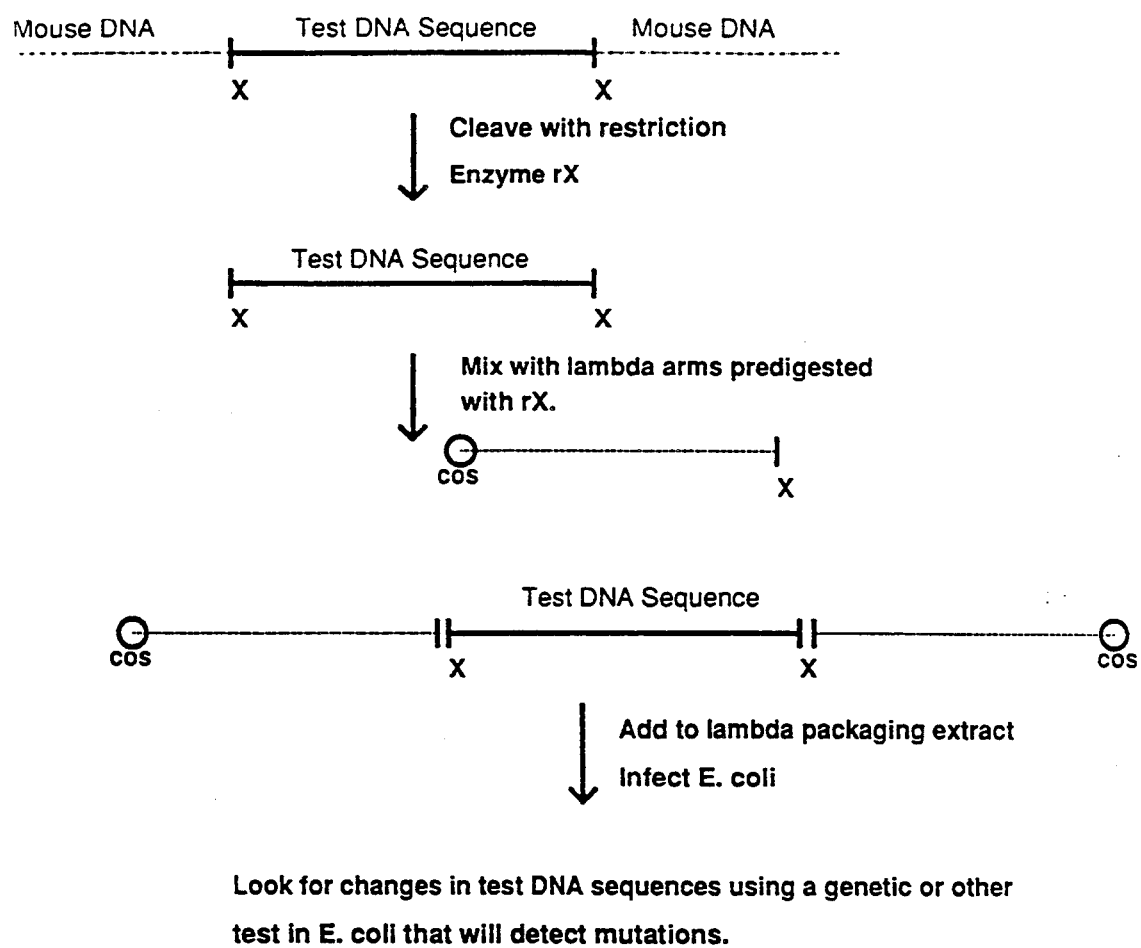
FIG. 2 illustrates an alternative method for recovering the transgenic test DNA sequence.

The present invention involves the introduction of at least one copy of at least one target DNA sequence into the cells of a non-human animal that is then bred to produce test animals. This test transgenic animal is then exposed to an agent that is suspected to be mutagenic. The target test DNA sequence is subsequently recovered from individual tissues of the transgenic animal and is transferred into a microorganism, where it can be assayed for mutations, allowing rapid examination of multiple tissue specific genetic mutations.

Theoretically, any animal suitable for mutagenic testing may be used as the starting organism. In order to allow for ubiquitous insertion of the novel test sequence, single cell animal embryos can be harvested, although there may be other cells facilitating the uptake and ultimate ubiquitous presence of the marker DNA in every cell of a differentiated animal.

A test DNA sequence must be prepared for insertion into the animal. Any number or variety of sequences coding for a phenotype or genotype that is easily detectable upon mutation may be used. A vector capable of facilitating the recovery of the test DNA sequence from the host animal cells, and capable of allowing autonomous replication and expression of the sequence in the anticipated bacterial host may be used as a carrier for the target test DNA sequence. Thus, the construct for such a vector and insert should contain, at least, regions that allow insertion into and excision from the animal host genome, and regions that allow autonomous replication in the bacterial host cell, as well as regions that allow expression and assay of the test DNA sequence. If integration into the host genome is not required, desired regions that allow for replication of the test DNA sequence in the animal host cells should be present. Elbrecht, A., DeMayo, F. J., Tsai, M., and O'Malley, B. W. (1987). Episomal maintenance of a bovine papilloma virus vector in transgenic mice. Mol. Cell. Biol. 7:1276–1279.

A next step involves transforming the host animal with the test DNA sequence, so as to provide the stable presence of the test sequence throughout cells of the differentiated animal. Typically, this involves the integration of the test DNA sequence into the animal host genome, although methods that allow the test sequence to be stably and heritably present through the use of autonomously replicating vectors may also be useful. Elbrecht, A., DeMayo, F. J., Tsai, M., and O'Malley, B. W. (1987). Episomal maintenance of a bovine papilloma virus vector in transgenic mice. Mol. Cell. Biol. 7:1276–1279. The vector containing the test DNA sequence must be physically introduced into the animal. At the cellular level, this may be accomplished using the techniques of microinjection, electroporation, dielectrophoresis or various chemically mediated transformation techniques, all of which are well known in the art. At the differentiated tissue level, other techniques may be necessary.

Once the test DNA sequence has been introduced and has integrated into the genome or cell, the transgenic cells must be allowed to differentiate into a whole organism. This may be done, for example, by embryo implantation into pseudopregnant females, or by other techniques allowing maturation of transgenic embryos. Once such maturation and differentiation has occurred, the animal is assayed for the presence of the test DNA sequence. Typically this involves removing small portions of tissue from the animal and using DNA hybridization assay techniques to detect the presence of the test DNA sequence.

If the animal carries the test DNA sequence, the animal may be bred and its offspring that carry the transgenic DNA sequence may be used for studies of mutagenesis. The test animal is exposed to the agent or substance in question under appropriate conditions. Such conditions will depend, for example, on the nature of the agent or substance, the purpose of the mutagenesis study and the type of data desired.

After exposure of test transgenic animals to the agent to be tested under the desired conditions, tissues are removed from the test animal. Because the test DNA sequence is present in essentially all tissues, the tissue type tested is not limited by the process of insertion of the test sequence. Any desired tissue may be removed. Genomic DNA is purified from the tissue.

The target test DNA sequence which is integrated is rescued from the total genomic DNA of the host. This may be accomplished by excising it from the host genome or by any procedures allowing separation by size, weight or charge density. The method of rescue is dependent upon whether test DNA sequence is inserted into the genome, and whether flanking regions allow for excision, or whether the test DNA sequence is part of an autonomously replicating element allowing for separation techniques.

The rescued test DNA sequences are then transferred into and expressed by microorganisms appropriate for large scale screening techniques. Typically this involves excising the test DNA sequence vector from the genomic DNA by packaging the test DNA sequence with bacteriophage packaging techniques, but it may require ligating the test DNA sequence into an appropriate vector or merely require direct transformation into a microorganism.

The microorganisms containing the test DNA sequence vector are then grown on indicator plates or in selective media. Those organisms having a phenotype indicating mutation of the test DNA sequence may be considered to contain a mutated test DNA sequence. The ratio of those organisms expressing mutated phenotype of test sequences to the total number of organisms containing the test DNA sequence is a measure of the mutagenicity of the agent and metabolites of it present in the tested tissue.

DESCRIPTION OF THE PREFERRED EMBODIMENTS

The following description provides details of the manner in which the embodiments of the present invention may be made and used in order to achieve the rapid recovery and examination of test DNA sequences from transgenic animals. This description, while exemplary of the present invention, is not to be construed as specifically limiting the invention. Such variations and equivalents, now known or later developed, that would be within the purview of one skilled in this art are to be considered to fall within the scope of this invention, which is limited only as set forth by the appended claims.

A. Creation of a Transgenic Animal

Mice were used as the test animal. Single cell mouse embryos were harvested from female mice that were impregnated the evening before. The embryos were treated with hyaluronidase and briefly cultured in M16 medium. The embryos were transferred to M2 medium on a microscope glass depression slide. The embryos were observed with a 40 X objective and a 10 X eyepiece using a Nikon Diaphot microscope equipped with Hoffman optics. The embryos were held in place with a holding pipet that had been rounded with a microforge. The positions of both the holding pipets and the injection pipets were controlled with micromanipulators. DNA as described below was loaded in the injection pipet at a concentration of 1 to 10 micrograms per milliliter. Approximately one picoliter, as judged by a refractile change of the pronucleus, of DNA solution was injected into the male pronucleus.

After DNA injection, the embryos were transferred to M16 medium and incubated at 37° C. in a 5% $CO_2$ atmosphere for one to two hours. Lysed embryos were discarded and embryos that appeared normal were transferred to one of the fallopian tubes of pseudopregnant foster mothers. The transfers were performed under a dissecting microscope using general anesthesia (avertin).

After birth, newborn mice were kept with their foster mothers for 2 weeks, at which point they were then weaned and screened for DNA integration. A 2 cm portion of the tail was removed and homogenized in 2 ml of a solution of 0.1M NaCl, 50 mM Tris-HCl, pH 7.5, 1 mM EDTA for short duration, but long enough to disrupt cell and nuclear membranes. The homogenized tissue was treated with 50 U/ml RNaseA and 0.1% SDS for 15 minutes at 37° C. The mixture was exposed to Proteinase K digestion for 3 hours at 55° C. followed by three extractions with phenol/chloroform. DNA was then precipitated by the addition of ethanol. After resuspending the precipitated DNA in 10 mM Tris pH 8.0, 0.5 mM EDTA, some of it was digested with BamHI endonuclease and electrophoresed through an 0.8% agarose gel. The DNA was denatured by soaking the gel in 1.5M NaCl, 0.5M NaOH for one hour and then neutralizing the DNA by soaking it in 1.5M NaCl, 0.5M Tris, pH 7.4 for 30 minutes. The gel was then soaked in 10 X SSC for one hour. The DNA was then transferred from the gel onto a nitrocellulose filter by the method of Southern, as described in Maniatis, T., Fritsch, E. F., Sambrook, J., *Molecular Cloning, A Laboratory Manual*, pp. 109–110, 383–389 (Cold Spring Harbor, N. Y. 1982).

The filter with transferred DNA was hybridized overnight with $^{32}P$ labeled lambda DNA prepared, according to standard procedures, by the method of nick translation. Maniatis, supra. Following this overnight hybridization, the filter was washed in 0.1×SSC, 0.1% SDS at 50° C. and Kodak XAR film was exposed to it in order to identify lambda DNA present within the mouse genome. Lambda DNA, used as standards, that had been electrophoresed alongside the mouse genomic DNA were compared in intensity to the transgenic mouse DNA hybridized to the $^{32}P$ labeled lambda DNA to estimate copy number. Numerous transgenic animals have been produced and identified by this technique and most of them transmit the integrated DNA to their offspring, demonstrating germ line integration.

The test sequence DNA can, theoretically, contain any number or variety of genes or other identifiable test DNA sequences. In the prototype described herein, an *E. coli* bacteriophage lambda genome has been engineered to carry a beta-galactosidase test DNA sequence. The genotype of the modified lambda genome L2B is lac5 delta (shindIII lambda 2°–3°) srI lambda 3°–5° cI857 sXhI lambda 1° sScII lambda 4°. Before injecting it into mouse embryos, this lambda DNA was diluted to a concentration of 10 micrograms per milliliter and the cos ends were annealed and ligated under conditions predominantly forming circular lambda phage monomers. Maniatis, supra.

Newborn mice were tested for the presence of the test DNA sequence by the tail-blotting procedure. Hogan, et al., *Manipulating the Mouse Embroyo: A Laboratory Manual*, pp. 174–183 (Cold Spring Harbor Laboratory, 1986). Several of the newborns were found to carry the test DNA sequence in DNA isolated from their tails. Eight weeks after birth these transgenic mice were mated and their progeny were examined for the test DNA sequence. Approximately 50% of the resulting offspring carried the test DNA sequence, demonstrating that the original transgenic mice carried the test DNA sequence in their germ line and that this sequence was inherited normally. While transgenic lines having approximately one copy of the test DNA sequence per cell can be obtained, lines having at least about 5–10 copies per cell are preferred. This is believed to make the rescue procedure more efficient. Mouse embryos of a progeny of a transgenic mouse produced and identified by this technique and containing the beta-galactosidase test DNA sequence have been deposited with the American Type Culture Collection (ATCC; Rockville, Md.) having an ATCC accession number 72011.

B. Mutagenesis Testing Using Transgenic Animals Carrying Test DNA Sequence

The target vector lambda L2B can be used initially to establish background mutagenesis rates within transgenic mouse strains. A variation of L2B may be constructed that also contains a plasmid sequence that can be readily excised from the lambda phage and contains the Lac I gene. This variation may have two advantages. First, mutations will appear as blue plaques on a white background in the presence of X-gal (5-bromo-4-chloro-3-indolyl-$\beta$-D-galactopyranoside) without IPTG (isopropyl$\beta$-D-thiogalactopyranoside). This should aid in the identification of mutations. Second, the blue plaques will represent Lac I mutations which may be isolated and rapidly assessed.

When genomic DNA is purified from any tissue of the transgenic mouse, the test DNA sequence can be found within the genomic DNA. Since the test DNA sequence is contained within a lambda phage genome, it can be excised away from the remainder of the genomic DNA by using a lambda phage packaging extract. Approximately 10 micrograms of genomic DNA (isolated as described above) is added to 100 microliters of lambda phage packaging extract (Gigapack Gold, Stratagene Cloning Systems, San Diego, Calif.) and incubated for 2 hours at 23° C. The reaction is then diluted with 5000 microliters of SM (100 mM NaCl, 8 mM MgSO$_4$ 7H$_2$O, 50 mM. Tris, pH 7.5, 0.01% gelatin) and 200 microliters of chloroform. The reaction mixture is then added to $2 \times 10^9$ $\beta$-galactosidase deficient *E. coli* that have been grown in the presence of 0.2% maltose and 10 mM MgCl$_2$. After incubating at 37° C. for 15 minutes, 7 milliliters of liquid top agarose (85 mM NaCl, 8 mM MgSo$_4$ 7H$_2$O, 5 g/l yeast extract, 10 g/l NZamine, 0.7% agarose at 48° C.) is added and the mixture is poured onto a petri dish containing nutrient agar supplemented with X-Gal (4 mg/ml) and IPTG (1 mM). The plates are incubated overnight at 37° C. Rescued test lac I sequences appear as plaques of lysed bacteria on a confluent "lawn" of *E. coli*.

In the presence of X-gal (5-bromo-4-chloro-3-indoyl-$\beta$-D-galactoside) and IPTG, the phage plaques turn blue if the beta-galactosidase sequence within the lambda genome has not mutated. However, a white plaque on the petri dish is evidence that a mutation in the beta-galactosidase sequence has, for example, altered the reading fram, altered essential codons, or have created stop codons in the sequence. These white plaques will be scored as positive for mutations and they can be plaque purified and saved for further analysis. The ratio of white to blue plaques minus background will indicate the mutagenesis potency of the agent being tested when compared with DNA extracted from mice that have not been treated with potentially mutagenic agents.

In the embodiment described here, rescue of the marker DNA sequence is possible because it is contained within a lambda bacteriophage genome. The entire lambda bacteriophage genome is excised from the mouse chromosome by the in vitro packaging extract. The packaging extract recognizes the cos sites of the integrated lambda DNA and packages the sequences between the cos sites into lambda phage particles, as shown in FIG. 1.

It is anticipated that test DNA sequence rescue efficiency can be influenced by the state of CpG methylation in the mouse chromosome. Highly methylated DNA may not be efficiently excised by lambda packaging extract, presumably because of inhibition of cleavage at the cos sites. It is anticipated that this can be alleviated by placing transcriptional enhancers, promoters and/or other regions of the DNA which inhibit methylation near the cos site to reduce CpG methylation. The drug 5'-azacytidine can also be used to reduce the level of DNA methylation in the target cells prior to DNA purification and rescue. Jaenisch, R., et al., *Proc. Natl. Acad. Sci. USA* 82:1451–1455 (1985). In such a procedure, fibroblast cell lines are obtained from organisms containing the test DNA sequence of interest. Adams, R. L. P., *Cell Culture for Biochemists*, pages 68–83 (1980 Elselvier/North Holland Biomedical Press). The cells are exposed in vitro at 37° C., with 50 $\mu$m 5'azacytidine supplementing the culture medium. Upon DNA replication, the daughter DNA loses its CgG methylation, which eliminates the methylation of cos sites in the target vector, where the target vector is a lambda phage. The DNA from these fibroblasts is then exposed to in vitro packaging extract, as previously described.

Alternatively, organisms containing the test DNA sequence can be directly injected with a 1 mg/ml solution of 5'-azacytidine in 0.15M NaCl. This is done over a period of at least 4 days, with a total of 400 $\mu$g administered. Jaenisch, supra. After this treatment, DNA can be extracted from various tissues and packaged as before.

Of course, any number or variety of test DNA sequence or gene can be inserted between lambda cos sites. The in vitro packaging extract would still excise the DNA between the cos sites and insert it into a lambda phage particle. Thus, a variety of recombinant lambda genomes or cosmids may be used for this excision event.

The embodiment described above utilizes the *E. coli* beta-galactosidase gene as a test DNA sequence, which allows phenotypes that are positive and negative for mutation to be observed. Other potential test DNA sequences include (but are not limited to): the lac I repressor, the cI repressor, any antibiotic resistance gene sequence (ampicillin, kanamycin, tetracycline, neomycin, chloroamphenicol, etc.), the lambda red and gam gene sequences, a thymidine kinase gene sequence, a xanthine-guanine phosphoribosyl transferase gene sequence, sequences that code for restriction enzymes or methylation enzymes, a gene sequence that codes for luciferase, and/or a tRNA stop codon or frameshift suppressor gene sequence.

Even more general models can be made that eliminate the cos sites, although the excision mechanism now becomes different. By bracketing the test DNA sequence(s) with convenient restriction sites, as shown in FIG. 2, the test sequence(s) can be separated away from the mouse DNA with restriction enzymes and subsequently ligated with lambda or cosmid vectors which contain cos sites. Background can be reduced in such a system by including with the test DNA sequences a sequence that is necessary for lambda phage replication, which is then cloned with the test DNA sequence into a lambda genome deficient or defective in that sequence.

We claim:

1. A transgenic mouse whose somatic and germ cells contain the beta-galactosidase gene flanked by the bacteriophage lambda cos sites, and the expression of said beta-galactosidase gene being capable of detection in *E. coli*.

2. The transgenic mouse of claim 1, wherein said beta-galactosidase gene is carried in a modified bacteriophage lambda genome L2B.

3. The transgenic mouse of claim 2 which is derived from a mouse embryo deposited with the American Type Culture Collection and having an ATCC accession number 72011.

* * * * *